(12) United States Patent
Buchalter

(10) Patent No.: US 7,351,747 B2
(45) Date of Patent: Apr. 1, 2008

(54) SKIN TREATMENT FOR RELIEF OF ITCH

(76) Inventor: Gilbert Buchalter, 28 Mountainview Rd., Millburn, NJ (US) 07041

( * ) Notice: Subject to any disclaimer, the term of this patent is extended or adjusted under 35 U.S.C. 154(b) by 689 days.

(21) Appl. No.: 10/337,131

(22) Filed: Jan. 6, 2003

(65) Prior Publication Data

US 2004/0131696 A1    Jul. 8, 2004

(51) Int. Cl.
*A61K 33/06* (2006.01)
*A61K 33/00* (2006.01)

(52) U.S. Cl. .................. 514/887; 424/443; 424/66; 424/68; 514/886

(58) Field of Classification Search .............. 424/68, 424/66, 45, 400, 402; 514/886
See application file for complete search history.

(56) References Cited

U.S. PATENT DOCUMENTS

| | | | |
|---|---|---|---|
| 3,749,772 A | 7/1973 | Cardarelli et al. | |
| 3,862,331 A | 1/1975 | Crary | |
| 3,875,301 A | 4/1975 | Windheuser | |
| 3,922,342 A | 11/1975 | Rathbun | |
| 4,053,630 A * | 10/1977 | Yu et al. ................. | 514/502 |
| 4,152,416 A * | 5/1979 | Spitzer et al. ............... | 424/46 |
| 4,663,151 A * | 5/1987 | Waali ........................ | 424/45 |
| 4,937,069 A * | 6/1990 | Shin ........................... | 424/66 |
| 5,376,362 A * | 12/1994 | Murphy et al. ............. | 424/66 |
| 5,585,093 A * | 12/1996 | Murphy ...................... | 424/65 |
| 5,667,790 A | 9/1997 | Sellers, Jr. | |
| 5,750,096 A * | 5/1998 | Guskey ...................... | 424/65 |
| 5,866,143 A | 2/1999 | Elkhoury | |
| 6,096,298 A | 8/2000 | Swaile | |
| 6,499,626 B1 * | 12/2002 | Julius ......................... | 221/63 |

* cited by examiner

*Primary Examiner*—Michael P. Woodward
*Assistant Examiner*—M. Mercier
(74) *Attorney, Agent, or Firm*—Lerner, David, Littenberg, Krumholz & Mentlik, LLP

(57) ABSTRACT

A method for treating skin itch in an individual in need of such treatment, by topically administering an amount effective for relieving said itch of an additive selected from the group consisting of (a) aluminum chlorohydrates; (b) aluminum zirconium chlorohydrates; (c) chlorohydrates of aluminum and aluminum zirconium, each complexed with polyalkylene glycol; (d) chlorohydrates of aluminum and aluminum zirconium, wherein in each of said chlorohydrates some of the water of hydration has been replaced by glycine; (e) aluminum chloride hydrate; and mixtures thereof. In particular, a spray comprising aluminum chlorohydrate aqueous composition is applied to the affected surface area of the skin to effect relief from itching.

22 Claims, No Drawings

SKIN TREATMENT FOR RELIEF OF ITCH

BACKGROUND OF THE INVENTION

This invention relates to a method for treating skin itch including itch due to a nonspecific cause. More specifically, the invention relates the use of compounds such as aluminum chlorohydrate in a composition with a carrier to treat skin itch by application of the composition to the surface of the skin.

Skin itch can be caused by various agents, e.g., synthetic or natural chemicals, or it may arise as a result of ambient conditions such as heat and humidity leading to sweating; conversely, it may be caused by excessive ambient dryness. Itch can also be caused by skin contact with an irritant. In other instances a specific cause for skin itch is not conveniently identified; in such circumstances the condition is referred to herein as nonspecific itch. While various causes and mechanisms of itch have been studied, it is not yet fully understood. In those circumstances where skin itch is associated with a specific medical condition, the best treatment is to treat the underlying disease. However, if the cause has not been identified or if there is no specific treatment available that also relieves the itch, various therapies and compositions have been used in an effort to provide relief, including antihistamines, steroids, capsaicin, moisturizers, menthol-phenol preparations, and even the simple application of a cool, moist cloth.

U.S. Pat. No. 3,922,342 to Rathbun describes a method for the removal from the skin of the active phenolic compounds of an individual exposed to the oil of poison ivy and oak utilizing a hydrophilic anion exchange material applied topically to the affected skin area in a suitable carrier. After a sufficient contact time, the anion exchange material is removed and discarded. The treated area is rinsed with water and dried.

U.S. Pat. No. 3,875,301 to Windheuser describes a process for treating the skin and relieving the symptoms caused by poison oak or ivy by the topical application of certain tetraalkyl diamines.

U.S. Pat. No. 3,862,331 to Crary describes a process for treating the skin and relieving the symptoms caused by poison oak or ivy by the topical application of 2-butanone.

U.S. Pat. No. 3,749,772 to Cardarelli et al. describes a composition that prevents skin irritation caused by contact with poison ivy or oak based upon a film-forming acrylic polymer and including a crosslinking agent, so that upon application in a solvent carrier to the skin a protective membrane is formed.

U.S. Pat. No. 4,663,151 to Waali, describes a method for preventing rather than relieving symptoms of dermatitis or skin irritation caused by exposure to alkyl catechols, the active agents in urushiol oil. The method involves application of an aluminum chlorohydrate composition in order to complex with and inactivate the alkyl catechols.

U.S. Pat. No. 5,667,790 to Sellers, Jr. describes a method of treating skin affected by acne or rosacea comprising the application of a finely divided aluminum halide salt dispersed in a carrier to the area of skin affected by acne or rosacea, allowing the composition to remain on the skin for a period of time and washing off the composition.

U.S. Pat. No. 5,866,143 to Elkhoury describes the topical application of an opioid analgesic drug to an area of itching skin in a patient by mixing the opioid drug with a carrying agent and applying it to the affected area. While the amount of opioid used is ineffective for production of a systemic effect, the use of an opioid necessarily requires careful supervision.

While the art has provided various methods and compositions for preventing and relieving itch from various causes, the need still exists for a method of relieving itch that is effective, simple, and inexpensive without causing any major detrimental side effects in the individual.

Accordingly, it is one object of the present invention to provide a method of relieving skin itch in an individual.

Another object of the present invention herein is to provide a new method of relieving skin itch for which no specific cause may be apparent by the topical application of an efficacious composition to the skin.

A still further object of this invention is to provide a method of treating skin itch by the topical application to the affected area of a composition comprising a compound such as aluminum chlorohydrate in a carrier.

The achievement of these and other objects will be apparent from the following description of the subject invention.

SUMMARY OF THE INVENTION

These and other objects are achieved by treating skin itch in an individual in need of such treatment, comprising topically administering an itch relieving agent or additive in a carrier. Typically, the agent is present in an amount effective for relieving the itch and is selected from the group consisting of (a) aluminum chlorohydrates; (b) aluminum zirconium chlorohydrates; (c) chlorohydrates of aluminum and aluminum zirconium, each complexed with polyalkylene glycol; (d) chlorohydrates of aluminum and aluminum zirconium, wherein in each of said chlorohydrates some of the water of hydration has been replaced by glycine; (e) aluminum chloride hydrate; and mixtures thereof. Specifically, this invention relates to a method of treating skin itch due to various causes which comprises the topical application to exposed skin of an efficacious amount of aluminum chlorohydrate compound in an appropriate carrier.

In another embodiment, this invention relates to a method of treating skin itch which comprises the application of an efficacious amount of an additive such as aluminum chlorohydrate, or equivalent compound, to the skin using a spray, lotion or cream in which the additive is present.

In a still further embodiment, this invention relates to a method of treating skin itch which comprises the application of an efficacious amount of an additive such as aluminum chlorohydrate, or equivalent compound, to the skin using a wipe or cloth on or in which the additive is present.

DETAILED DESCRIPTION OF THE INVENTION

This invention relates to a method of treating skin itch in persons or animals due to various causes, such causes being identified or not. Specifically, this invention is directed to the use of an efficacious amount of an aluminum chlorohydrate-containing compound to treat skin itch. For purposes of the present invention, reference to aluminum chlorohydrate and aluminum chlorohydrate is equivalent. Typically, the aluminum chlorohydrate is commercially available or can be prepared by art-recognized procedures from known compounds or intermediates readily available or prepared by known reaction schemes. Aluminum chlorohydrate is a common ingredient in antiperspirant compositions, but its mechanism of action has not been fully established. The following are aluminum chlorohydrate-containing compounds and equivalents thereto suitable for use in the present invention: aluminum chlorohydrates including aluminum chlorohydrate, aluminum sesquicholorhydrate and aluminum dichlorohydrate; aluminum zirconium chlorohydrates including aluminum zirconium octachlorohydrate, aluminum zirconium pentachlorohydrate, aluminum zirconium tetrachlorohydrate and aluminum zirconium trichlorohydrate; aluminum chloride hydrate; and other aluminum salts, provided that such other salts are not skin irritants at concentrations suitable for use in the present invention and do not cause other adverse side effects. Also useful in the present invention are partially dehydrated derivatives of the chlorohydrates of aluminum and aluminum zirconium, each complexed with polyalkylene glycol, for example polyethylene glycol or propylene glycol, or in which some of the water of hydration has been replaced by glycine. Furthermore, in the aluminum zirconium chlorohydrates the aluminum to zirconium ratio can be variable. For convenience of reference herein these compounds are referred to as chlorohydrates. Preferably, the chlorohydrate compound or active ingredient is aluminum chlorohydrate.

It is contemplated that the compound of the present invention can be applied topically to the skin where itch is experienced. The active ingredient is generally applied to the skin as a composition in combination with any of the described carriers in a suitable form for topical application. Topical application can be either in non-sprayable or sprayable form.

Carrier materials suitable for use in the instant compositions include those well-known for use in the cosmetic art as bases for ointments, lotions, salves, gels, aerosols, and the like. Suitable carriers include, for example, water, and various organic liquids such as alcohols, glycols, polyalkylene glycols, esters, amides, liquid lanolin and lanolin derivatives, and like materials commonly employed in cosmetic compositions; a comprehensive list of carriers can be found, for example, in U.S. Pat. No. 6,096,298, incorporated herein by reference to the extent permitted. Examples of carriers useful herein include alcohols, including both monohydric and polyhydric alcohols, e.g., ethanol, isopropanol, glycerol, sorbitol, 2-methoxyethanol, various glycols including ethylene and polyethylene glycols, propylene and polypropylene glycols, hexylene glycol, and mannitol; ethers such as diethyl or dipropyl ether; higher molecular weight compounds including polyethylene glycols and methoxypolyoxyethylenes (referred to as carbowax and having molecular weights ranging from about 200 to about 20,000); polyoxyethylene glycerols, polyoxyethylene sorbitols, and stearoyl diacetin. Emulsions such as cold cream bases can also be used.

The carrier for spray or direct liquid application can include a skin compatible, cosmetically acceptable liquid alcohol containing from about 2 to about 6 carbon atoms. Mixtures comprising from about 0% to 80% by weight or more of water and about 20% to 100% by weight of said $C_2$ to $C_6$ alcohols are also suitable. Suitable alcohols include ethanol, isopropanol, hexanol, and the like and mixtures thereof. An especially preferred carrier is water. Alternative carriers for the present application include those in which the additive, e.g., aluminum chlorohydrate, is soluble and/or dispersible, for example, water-ethanol (ethyl alcohol) mixtures at a weight ratio range of from about 1:20 to about 5:1.

Non-sprayable forms can be semi-solid or fluid forms comprising a carrier typical of such topical applications. Suitable formulations include, but are not limited to, solutions, suspensions, dispersions, emulsions, creams, ointments, liniments, salves and the like. If desired, these may be sterilized or mixed with auxiliary agents, e.g., preservatives, stabilizers, antioxidants, wetting agents, buffers or salts and the like. Preferred vehicles for non-sprayable topical preparations include ointment bases, e.g., polyethylene glycol-1000 (PEG-1000); creams, e.g., HEB cream (Barnes-Hind Co.); and gels, e.g., K-Y gel (Johnson & Johnson) and the like. HEB Cream is a combination of mineral oil, white petrolatum, stearyl alcohol, cetyl alcohol, sodium laurylsulfate, methylparaben and propylparaben. K-Y gel is a combination of carboxymethylcellulose, sodium alginate and a small amount of EDTA in water. Topical preparations may also contain emollients and/or humectants to enhance their performance and acceptability.

Also suitable for topical application are sprayable preparations, including aerosol sprays, wherein the chlorohydrate compound, preferably in combination with a liquid inert carrier material, is packaged in a squeeze bottle, a pump bottle or in admixture with a pressurized volatile, typically gaseous, propellant, e.g., a halogenated hydrocarbon, a $C_1$ to about $C_4$ alkane chlorofluorocarbon or any other environmentally acceptable volatile propellant. Suitable halogenated hydrocarbons include 1,1-difluoroethane, mixtures of trichlorofluoroethane and dichlorodifluoromethane and mixtures thereof. Suitable volatile alkanes useful as propellants include methane, propane, butane and mixtures thereof; incorporation of a suitable amount of methyl chloride can reduce their fire risk. Also useful is dimethyl ether, alone or in admixture with water. Alternatively, carbon dioxide generated in situ can be used as a propellant. The aerosol or spray preparations can contain stabilizers, preservatives, buffers, surfactants, perfumes and/or antioxidants in addition to the chlorohydrate compounds of the invention, with the same proviso as noted above with regard to limited use of such additional additives.

An alternative method of applying the composition of the present invention is the utilization of a "wet wipe." Such an applicator has the added convenience of portability since such wipes are typically provided in a tear-open foil or pouch container. The container can include a single wipe or multiple wipes for added convenience, particularly if, in the latter case, the container can be closed or resealed. Wet wipes are well known in the art and are used to provide various ingredients for application to the skin, for example, sun screens, moisturizers, insect repellants, lotions for dry skin, lubricants for shaving, etc. The wipes are typically treated cloths and comprise materials such as cellulosic fibrous sheet, non-woven fabric or porous sheet that is wetted with an aqueous composition of water soluble or water dispersible ingredients. Useful materials include paper, air-laid and non-woven webs, melt blown, spun-bonded and spun-lace webs as well as foam sheets. Fibers can be natural or synthetic and combinations thereof depending on the attributes needed and the method of forming the web or wipe. Techniques for moistening the wipes and packaging them in moisture impervious packages are well known in the art and need not be described herein.

Alternatively, treated sheets, tissues, cloths or articles comprising the composition of the present invention can be delivered from a sequential dispenser, in which articles are provided as individual interleaved or separably connected sheets and can pop-up from the dispenser when the preceding article is removed. Suitable containers preferable include a closure or lid for the sheet dispenser opening in order to reduce the loss of liquid by evaporation or otherwise. Dispensers for such articles typically have a box-like shape. The dispenser has an opening, typically at the top, through which individual articles or sheets are removed by the user. The desire for increased convenience has led to development of sequential or "pop-up" dispensers. In a pop-up dispenser, a sheet usually extends through an opening to an elevation above that of the dispenser. The user grasps the exposed portion of the sheet, without the necessity of inserting fingers through the opening. In pop-up dispensing, each sheet has a leading portion that is first to pass through the opening, and a trailing portion that later passes through the opening. In an interleaved arrangement, the trailing portion of a first sheet to be dispensed overlaps the leading portion of the next sheet to be dispensed. As the first sheet is withdrawn by the user, the leading portion of the next tissue is pulled through the opening for later dispensing. The sheets are folded against one another in a variety of configurations so that the friction of the trailing portion of the withdrawn sheet against the succeeding sheet pulls the leading portion of the succeeding sheet through the opening. Such constructions and dispensers are well known in the art and are typically used in connection with dry or liquid treated sheets, including, for example, tissues. Such dispensers are suitable for use herein and, in view of their well-known characteristics, need not be described in further detail; see, e.g., U.S. Pat. No. 6,499,626 to R. Julius, incorporated herein by reference to the extent permitted.

The use of an effective amount of at least one aluminum chlorhydrate containing compound or aluminum salt as described above will relieve itching of the skin. The concentration of chlorhydrate compound, for example, aluminum chlorhydrate, employed herein from about 1 wt. % to about 50 wt. % of the topical composition and can range from about 2% wt. to about 40 wt. %; preferably from about 5 wt. % to about 30 wt. %; more preferably from about 10 wt. % to about 25 wt. %; for example, from about 15 wt. % to about to about 20 wt. % of the topical composition.

The compositions herein can also include various agents and ingredients commonly employed in dermatological and cosmetic ointments and lotions. For example, thickening agents such as carboxymethylcellulose and clays, coloring agents and the like can be present in the compositions to provide a more pleasing aesthetic aspect. However, since the cause of the skin itch may be unidentified, it is preferred to use the fewest number of additives in addition to the active chlorhydrate compound in order to avoid unintended allergic or irritating effects.

In view of the considerable convenience, ease of application and lack of adverse side effects associated with the composition of the present invention, an individual experiencing skin itch can continue application of the composition to the skin on a periodic or continual basis in order to maintain an acceptable level of relief.

Any range of numbers recited in the specification or paragraphs describing various aspects of the invention, such as that representing a particular set of properties, units of measure, conditions, physical states or percentages, is intended literally to incorporate expressly herein by reference or otherwise, any number falling within such range, including any subset of numbers or ranges subsumed within any range so recited. Furthermore, the term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, properties such as particle size, surface area, diameter, volume, bulk density, etc., that are outside of the range or different from a single value, will achieve the desired result, namely, the relief of itch. Alternatively stated, the term "about" encompasses greater and lesser values than those recited provided that the value of the relevant property or condition facilitates reasonably meeting the technologic objective(s) of the present invention, namely the relief of itch.

EXAMPLE 1

Three individuals, one male and two female adults, each complaining of skin itch of undetermined origin, were treated as follows. A composition was prepared at a concentration of aluminum chlorhydrate of about 10 to about 20 weight percent in water and further including a small quantity of a quaternary ammonium compound as a preservative. The composition was applied as an aerosol to the area of the skin exhibiting itching by use of a pump spray head mounted on a plastic bottle. Relief from itching was experienced within a few minutes and was reported to last about one day. No adverse side effects were reported.

EXAMPLE 2

An adult individual has applied 30% wt. of aluminum chlorhydrate in a topical cream to an area of the forearm experiencing itch. The aluminum chlorhydrate containing composition relieves the skin itch in the absence of any other active agent.

EXAMPLE 3

An adult female complains of itch on her legs. An application of 30% wt. of aluminum chlorhydrate in a lotion to the affected area relieves the itch within a few minutes and the relief continues for a period of about 24 hours.

EXAMPLE 4

An adult male complaining of itch on his forearms and legs applies an ointment composition including 25% wt. of aluminum zirconium chlorhydrate to the affected areas. Itch is relieved within minutes of the application and the relief continues for a period of about 24 hours.

EXAMPLE 5

An aqueous composition comprising aluminum chlorhydrate at a concentration of about 20 weight percent is applied to a synthetic fabric wipe and sealed in a tear-open pouch. Subsequently, an adult male experiencing itch on his forearms tears open the pouch and wipes the area of the skin with the moist wipe; the wipe and pouch are discarded after use. Relief from the itching is experienced within minutes and the relief lasts about a day.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

The invention claimed is:

1. A method of treating skin itch in an individual in need of such treatment, consisting essentially of topically administering an amount effective for relieving said itch of an additive selected from the group consisting of (a) aluminum chlorhydrates; (b) aluminum zirconium chlorhydrates; (c)

chlorohydrates of aluminum and aluminum zirconium, each complexed with polyalkylene glycol; (d) chlorohydrates of aluminum and aluminum zirconium, wherein in each of said chlorohydrates some of the water of hydration has been replaced by glycine; (e) aluminum chloride hydrate; and mixtures thereof; provided said itch is not caused by urushiol oil.

2. The method according to claim 1 wherein said aluminum chlorohydrates are selected from the group consisting of aluminum chlorohydrate, aluminum sesquichlorohydrate and aluminum dichlorohydrate; and said aluminum zirconium chlorohydrates are selected from the group consisting of aluminum zirconium octachlorohydrate, aluminum zirconium pentachlorohydrate, aluminum zirconium tetrachlorohydrate and aluminum zirconium trichlorohydrate.

3. The method according to claim 2 wherein said additive is aluminum chlorohydrate.

4. The method according to claim 3, wherein said aluminum chlorhydrate is admixed with a cosmetically acceptable carrying agent, said mixture comprising a composition suitable for topical administration.

5. The method according to claim 4, wherein said aluminum chlorhydrate is present at a concentration of from about 1 wt. % to about 50 wt. % of said composition.

6. The method according to claim 4, wherein said composition comprises a fluid selected from the group consisting of water, alcohol and mixtures thereof.

7. The method according to claim 5, wherein said aluminum chlorhydrate is dispersed or dissolved in said carrying agent.

8. The method according to claim 1 wherein said polyalkylene glycol is selected from the group consisting of polyethylene glycol and polypropylene glycol.

9. The method according to claim 4, wherein said carrying agent is in the form of a fluid.

10. The method of claim 9 wherein said fluid is selected from the group consisting of a liquid, a gel or a lotion.

11. The method of claim 9 wherein said composition is delivered from a container through a spray head by a method selected from the group consisting of (a) pumping; and (b) releasing a propellant previously admixed with said composition.

12. The method according to claim 11, wherein said propellant is selected from the group consisting of a halogenated hydrocarbon, air, a $C_1$-$C_4$ alkane and mixtures thereof.

13. The method according to claim 12 wherein said halogenated hydrocarbon is selected from the group consisting of (a) a mixture of trichlorofluoromethane and dichlorodifluoromethane; (b) 1,1-difluoroethane; and mixtures thereof.

14. The method according to claim 12 wherein said alkane is selected from the group consisting of methane, propane, butane and mixtures thereof.

15. The method according to claim 9 wherein said composition is delivered from a deformable or flexible container by squeezing said container.

16. The method according to claim 9 wherein said composition is applied to the skin by wiping with a sheet on which said composition is dispersed.

17. The method according to claim 16 wherein said sheet comprises natural or synthetic fibers.

18. The method according to claim 16 wherein said sheet is carried in a sealed pouch capable of being opened by the user prior to use of said sheet.

19. The method according to claim 4, wherein said carrying agent is in the form of a gel and is administered by spreading onto the skin of said individual.

20. The method according to claim 4, wherein said carrying agent is in the form of a cream or a lotion and is administered by spreading onto the skin of said individual.

21. The method according to claim 16 wherein said sheet is delivered from a dispenser comprising multiple sheets.

22. The method according to claim 21 wherein said dispenser provides for delivery of said sheet in pop-up fashion.

* * * * *